United States Patent [19]

Flowers

[11] Patent Number: 5,676,255
[45] Date of Patent: Oct. 14, 1997

[54] METHOD OF RECYCLING MEDICAL INSTRUMENTS

[75] Inventor: Jon Wade Flowers, Albuquerque, N. Mex.

[73] Assignee: Universal Recycling Inc., Albuquerque, N. Mex.

[21] Appl. No.: 508,793

[22] Filed: Jul. 28, 1995

[51] Int. Cl.⁶ ............................................. B03B 9/00
[52] U.S. Cl. ............................. 209/2; 209/3; 209/702
[58] Field of Search ........................... 209/702, 703, 209/2, 3, 3.1

[56] References Cited

U.S. PATENT DOCUMENTS 4,494,804  1/1985  O'Keeffe ..................... 209/703 X
5,117,982  6/1992  Shotthafer et al. ............. 209/702 X

FOREIGN PATENT DOCUMENTS 973122  8/1975  Canada ........................ 209/702

*Primary Examiner*—David H. Bollinger
*Attorney, Agent, or Firm*—Robert W. Becker & Associates

[57] ABSTRACT

A method of recycling medical instruments, especially surgical instruments. The decontaminated medical instruments are received and identified for processing. The analysis and construction of each type of instrument to identify the components and material compositions thereof are determined. A given type of instrument is then dismantled into pieces, which are then sorted by the material compositions thereof as ascertained in the previous determination of the analysis and construction of the instruments.

9 Claims, No Drawings

METHOD OF RECYCLING MEDICAL INSTRUMENTS

BACKGROUND OF THE INVENTION

The present invention relates to a method of recycling medical instruments, especially surgical instruments.

Medical instruments, such as surgical instruments, that are not allowed to be reused or that must for some other reason be disposed of or replaced are typically either incinerated or are prepared for disposal in landfills. Not only do these known procedures waste potentially recyclable material, but they also contribute to air pollution and/or to the rapid filling of landfills along with associated ground water pollution problems.

It is therefore the objective of the present invention to provide an alternative to incineration and land fill disposal of medical instruments, and in particular to provide for recycling of such medical instruments. The inventive method serves to reduce the potential liability of hospitals and other users of such instruments.

SUMMARY OF THE INVENTION

Pursuant to the inventive method, medical instruments received for processing are sorted by instrument type, if necessary; the analysis and construction of each type of instrument are determined to identify the components and material compositions thereof; a given type of instrument is dismantled into pieces; and the pieces are sorted by the material composition thereof.

The type of medical instruments under consideration must be very carefully accounted for. Before the instruments can be processed, they must be decontaminated, with such decontamination being certified. Thereupon, the instruments are closely tracked, for example by container tracking numbers and preferably by computer, throughout the entire recycling process, so that all instruments received for processing can be accounted for. This can be accomplished, for example, by weighing the instruments at the beginning of the process and again at the conclusion of the process.

When the decontaminated medical instruments are received for processing, several types of instruments are often mixed together. Thus, the first step in the recycling process would be to sort the instruments by type, if necessary. This not only facilitates the subsequent dismantling processes, but is also necessary in order to segregate the instruments by the types of material from which they are made. In this connection, for each type of instrument it is imperative that the analysis and construction of a given type of instrument be determined in order to identify not only the individual components thereof but also the material compositions of such components.

A given type of instrument can now be dismantled into pieces; it is to be understood that the term "pieces" is being used within the context of the instant application to refer not only to the individual components of the instrument, but possibly also merely to pieces thereof that result from the dismantling process itself. The pieces are then sorted in conformity with their material composition; different types of metals must be separated from one another, and different types of plastic must also be separated from one another. With respect to the various metal components, these can respectively be packaged for sale or for transport to a metal processor, where, for example, they might be melted down. The plastic pieces, on the other hand, are sorted by type, color and material composition and are then granulated, whereupon the granulate is packaged for sale. It should be noted that such granulation of the plastic parts is necessary since such parts must be "destroyed", in other words, they are not allowed to retain their original form.

The composition of the various medical and in particular surgical instruments that are handled by the inventive recycling process can be quite diverse and also quite complex. For example, a surgical instrument can be comprised of handles, triggers, levers, inner and outer couplings, knobs, shrouds, caps, and the like. Furthermore, the components of the instrument can comprise a number of different metals, rubber and plastic parts, including aluminum and stainless steel metal components, and engineering plastics such as polycarbonate, nylon, polyetherimide, polyethylene, polystyrene, acrylonitrile-butadiene-styrene, etc. plastic parts. Thus, it can be clearly seen that the step of determining the analysis and construction of a given type of instrument to identify the components and material compositions thereof is extremely critical. Manufacturers' data sheets, if available, are very helpful. Alternatively, the material compositions of the various components of the instruments can also be analyzed in the laboratory. In either case, a list of the components and material compositions thereof must be made for each type of instrument; such lists are preferably computerized.

A given type of instrument can now be dismantled into pieces, whereby the metal components generally maintain their form, whereas the plastic parts may fall apart or be broken apart during the dismantling process. In some cases, dismantling can be accomplished manually, with or without hand tools. In many situations, however, it is necessary to use more sophisticated equipment for the dismantling process. For example, anvils can be used to break apart the pieces, arbor and bearing presses can be used, lathes and cutters can be utilized, and appropriate dyes can also be made to receive the components to facilitate dismantling thereof.

The metal and plastic components and pieces must then be separated from one another, such as by magnets, shakers, optics, manually or any other suitable means. Whereas the metal components can be sold or disposed of in their original form, or can be sent to a smelter for further processing, the plastic components and pieces thereof must be granulated. Therefore, the plastic pieces are first separated by material compositions, type and color, and are then processed in a granulator in order to reduce them to the desired size.

The present invention is, of course, in no way restricted to the specific disclosure of the specification, but also encompasses any modifications within the scope of the appended claims.

What I claim is:

1. A method of recycling medical instruments, including the steps of:

receiving and identifying medical instruments for processing;

determining the analysis and construction of each type of instrument to identify the components and material compositions thereof;

dismantling a given type of instrument into pieces; and sorting said pieces by said material compositions thereof as ascertained in said determining step.

2. A method of recycling medical instruments according to claim 1, wherein said dismantling step comprises breaking down said instrument into its respective metal, plastic, and other material parts.

3. A method of recycling medical instruments according to claim 2, wherein said metal parts are separated in conformity with the material composition thereof.

4. A method of recycling medical instruments according to claim 2, wherein said plastic parts are separated in conformity with the material composition and color thereof.

5. A method of recycling medical instruments according to claim 4, wherein said plastic parts are granulated.

6. A method of recycling medical instruments according to claim 1, wherein said determining step comprises producing a listing of the exact components of said instrument as well as the material composition of each of said components.

7. A method of recycling medical instruments according to claim 1, wherein said dismantling step comprises the use of tools, presses and dies.

8. A method of recycling medical instruments according to claim 1, which includes the additional step of tracking said instruments throughout said process to ensure that all of said instruments are fully accounted for.

9. A method of recycling medical instruments according to claim 8, wherein said tracking step includes weighing said instruments at the beginning of said process and weighing said pieces thereof at the conclusion of said process.

* * * * *